United States Patent
Brady et al.

(10) Patent No.: US 10,004,464 B2
(45) Date of Patent: Jun. 26, 2018

(54) SYSTEM FOR IMPROVED COMPRESSIVE TOMOGRAPHY AND METHOD THEREFOR

(71) Applicant: Duke University, Durham, NC (US)

(72) Inventors: David Jones Brady, Durham, NC (US); Lawrence L. Carin, Chapel Hill, NC (US); Yan Kaganovsky, Durham, NC (US)

(73) Assignee: Duke University, Durham, NC (US)

( * ) Notice: Subject to any disclaimer, the term of this patent is extended or adjusted under 35 U.S.C. 154(b) by 120 days.

(21) Appl. No.: 14/764,435

(22) PCT Filed: Jan. 31, 2014

(86) PCT No.: PCT/US2014/014087
§ 371 (c)(1),
(2) Date: Jul. 29, 2015

(87) PCT Pub. No.: WO2014/121039
PCT Pub. Date: Aug. 7, 2014

(65) Prior Publication Data
US 2015/0351705 A1 Dec. 10, 2015

Related U.S. Application Data

(60) Provisional application No. 61/758,844, filed on Jan. 31, 2013.

(51) Int. Cl.
*G01N 23/00* (2006.01)
*A61B 6/03* (2006.01)
(Continued)

(52) U.S. Cl.
CPC ............ *A61B 6/032* (2013.01); *A61B 6/4007* (2013.01); *A61B 6/4085* (2013.01);
(Continued)

(58) Field of Classification Search
CPC ......... A61B 6/06; A61B 6/4291; A61B 6/484; G01T 1/295; G01N 23/04; G01N 2223/401
See application file for complete search history.

(56) References Cited

U.S. PATENT DOCUMENTS 3,971,065 A 7/1976 Bayer
5,048,959 A 9/1991 Morris et al.
(Continued)

FOREIGN PATENT DOCUMENTS

GB 2441162 A 2/2008
WO 2013103408 A1 7/2013
(Continued)

OTHER PUBLICATIONS

"International Application No. PCT/US2014/014087", "International Search Report and Written Opinion", Apr. 30, 2014, Publisher: ISA / KR, Published in: KR.
(Continued)

*Primary Examiner* — Hoon Song
(74) *Attorney, Agent, or Firm* — Kaplan Breyer Schwarz, LLP

(57) ABSTRACT

A method and system for forming tomographic images of an object using discrete, non-continuous illumination rays is disclosed. In some embodiments, coded apertures, collimation filters, or reference structures are used to filter the set of illumination rays from a two- or three-dimensional radiation signal, wherein the set of illumination rays are then used to interrogate the object. In some embodiments, the object is interrogated with a set of illumination rays that is continuous and a sparse array of detectors is used to sub-sample the illumination rays after they have passed through the object.

15 Claims, 11 Drawing Sheets

(51) Int. Cl.

| | | |
|---|---|---|
| *G06T 7/00* | (2017.01) | |
| *G06T 11/00* | (2006.01) | |
| *G01V 5/00* | (2006.01) | |
| *A61B 6/00* | (2006.01) | |
| *G01N 23/046* | (2018.01) | |

(52) U.S. Cl.
CPC .............. *A61B 6/4266* (2013.01); *A61B 6/52* (2013.01); *G01N 23/046* (2013.01); *G01V 5/005* (2013.01); *G06T 7/0012* (2013.01); *G06T 11/003* (2013.01); *G01N 2223/419* (2013.01); *G01N 2223/42* (2013.01); *G06T 2207/10081* (2013.01)

(56) References Cited

U.S. PATENT DOCUMENTS

| | | | |
|---|---|---|---|
| 5,157,298 | A | 10/1992 | Kawabata |
| 5,627,639 | A | 5/1997 | Mende et al. |
| 5,940,468 | A | 8/1999 | Huang et al. |
| 6,122,051 | A | 9/2000 | Ansley et al. |
| 6,205,195 | B1 | 3/2001 | Lanza |
| 6,392,235 | B1 | 5/2002 | Barrett et al. |
| 6,950,492 | B2 | 9/2005 | Besson |
| 7,265,698 | B2 | 9/2007 | Fackenthal et al. |
| 7,283,231 | B2 | 10/2007 | Brady et al. |
| 7,301,625 | B2 | 11/2007 | Brady et al. |
| 7,336,353 | B2 | 2/2008 | Brady et al. |
| 7,427,932 | B2 | 9/2008 | Brady et al. |
| 7,432,843 | B2 | 10/2008 | Brady et al. |
| 7,463,174 | B2 | 12/2008 | Brady et al. |
| 7,463,179 | B2 | 12/2008 | Brady et al. |
| 7,532,772 | B2 | 5/2009 | Brady |
| 7,573,579 | B2 | 8/2009 | Brady |
| 7,580,499 | B2 | 8/2009 | Van Stevendaal et al. |
| 7,583,783 | B2 | 9/2009 | Harding |
| 7,616,306 | B2 | 11/2009 | Brady et al. |
| 7,623,614 | B2 | 11/2009 | Shefsky |
| 7,835,495 | B2 | 11/2010 | Harding |
| 7,912,173 | B2 | 3/2011 | Brady |
| 8,149,400 | B2 | 4/2012 | Brady et al. |
| 8,338,793 | B2 | 12/2012 | DeVito |
| 8,553,222 | B2 | 10/2013 | Brady et al. |
| 8,928,988 | B1 | 1/2015 | Ford et al. |
| 8,932,894 | B2 | 1/2015 | Christophersen |
| 9,013,554 | B2 | 4/2015 | Brady et al. |
| 9,335,281 | B2 | 5/2016 | Marks et al. |
| 9,432,591 | B2 | 8/2016 | Brady et al. |
| 9,473,700 | B2 | 10/2016 | Cossairt et al. |
| 9,482,850 | B2 | 11/2016 | Ford et al. |
| 2002/0135885 | A1 | 9/2002 | Chen et al. |
| 2003/0095631 | A1 | 5/2003 | Rosner |
| 2004/0076319 | A1 | 4/2004 | Fauver et al. |
| 2005/0052751 | A1 | 3/2005 | Liu et al. |
| 2005/0174573 | A1 | 8/2005 | Harvey et al. |
| 2006/0038705 | A1 | 2/2006 | Brady et al. |
| 2006/0072109 | A1 | 4/2006 | Bodkin et al. |
| 2007/0047424 | A1 | 3/2007 | Wada et al. |
| 2007/0296965 | A1 | 12/2007 | Brady et al. |
| 2007/0296969 | A1 | 12/2007 | Goldstein et al. |
| 2008/0074663 | A1 | 3/2008 | Brady et al. |
| 2001/0190616 | A1* | 4/2008 | Shefsky ................. G01N 23/02 378/2 |
| 2008/0095298 | A1* | 4/2008 | Shefsky ................. G01N 23/02 378/2 |
| 2009/0201498 | A1 | 8/2009 | Raskar et al. |
| 2010/0177864 | A1* | 7/2010 | Donath .................. A61B 6/032 378/16 |
| 2010/0215142 | A1* | 8/2010 | Dafni ..................... A61B 6/032 378/19 |
| 2011/0019068 | A1 | 1/2011 | Chiu |
| 2011/0190616 | A1 | 8/2011 | Marwala et al. |
| 2011/0282181 | A1* | 11/2011 | Wang .................... A61B 5/0095 600/407 |
| 2012/0105844 | A1 | 5/2012 | Brady et al. |
| 2013/0021392 | A1 | 1/2013 | Travis |
| 2013/0250124 | A1 | 9/2013 | Furry |
| 2014/0247920 | A1 | 9/2014 | Marks et al. |
| 2015/0116553 | A1 | 4/2015 | Ford et al. |
| 2015/0207990 | A1 | 7/2015 | Ford et al. |
| 2016/0187269 | A1 | 6/2016 | Brady et al. |

FOREIGN PATENT DOCUMENTS

| | | |
|---|---|---|
| WO | 2014121039 A1 | 8/2014 |
| WO | 2015023741 A1 | 2/2015 |

OTHER PUBLICATIONS

Related International Application No. PCT/US2014/0140897, "International Preliminary Report on Patentability" dated Aug. 4, 2015.

Officer: Shane Thomas, "International Search Report & Written Opinion of the International Searching Authority"; Issued in related International Application No. PCT/US2012/058744, dated Jun. 17, 2013.

Athina Nickitas-Etienne, "International Preliminary Report on Patentability", issued in related International Application No. PCT/US2012/058744, dated Apr. 17, 2014.

"International Search Report and Written Opinion of the International Searching Authority", issued in International Application No. PCT/US2014/050872, dated Dec. 1, 2014.

Westmore, et al., "Angular-dependent coherent scatter measured with a diagnostic x-ray image intensifier-based imaging system", "Medical Physics", Feb. 19, 1996, pp. 723-733, vol. 23, No. 5, Publisher: American Association of Physicists in Medicine, Published in: CA.

Dicken, et al., "Combined X-ray diffraction and kinetic depth effect imaging", "Optics Express", Mar. 21, 2011, pp. 6406-6413, vol. 19, No. 7, Publisher: Optical Society of America.

Choi, et al., "Coded Aperture Computed Tomography", "Adaptive Coded Aperture Imagine, Non-Imaging, and Unconventional Imaging Sensor Systems", 2009, pp. 1-10, vol. 7468, No. 74680B, Publisher: SPIE; doi: 10.1117/12.825277.

Greenberg, et al., "Structured illumination for tomographic X-ray diffraction imaging", "Analyst", Dec. 4, 2013, pp. 709-713, vol. 139, Publisher: The Royal Society of Chemistry; DOI: 10.1039/c3an01641b.

Harding, et al., "Automatic detection of explosives in airline baggage using elastic X-ray scatter", "medicamundi", Jul. 1998, pp. 30-33, vol. 42, No. 2.

Maccabe, et al., "Pencil beam coded aperture x-ray scatter imaging", "Optics Express", Jul. 16, 2012, pp. 16310-16320, vol. 20, No. 15, Publisher: OSA, Published in: US.

Mrozack, et al., "Coded aperture spectroscopy with denoising through sparsity", "Optics Express", Jan. 16, 2012, pp. 2297-2309, vol. 20, No. 2, Publisher: OSA, Published in: US.

William Hadley Richardson, "Bayesian-Based Iterative Method of Image Restoration", Jan. 1972, pp. 55-59, vol. 62, No. 1, Publisher: Journal of the Optical Society of America, Published in: US.

Westmore, et al., "Tomographic imaging of the angular-dependent coherent-scatter cross section", "Medical Physics", Jan. 1997, pp. 1-10, vol. 24, No. 1, Publisher: American Association of Physicists in Medicine.

"Non-Final Office Action", Related U.S. Appl. No. 15/351,077, dated Mar. 23, 2017, 10 pp.

Officer Simin Baharlou "International Preliminary Report on Patentability", International Patent Application No. PCT/US2014/050872, dated Feb. 25, 2016, 10 pp.

"Non-Final Office Action", U.S. Appl. No. 13/340,893 dated Feb. 7, 2013, 11 pp.

"Non-Final Office Action", U.S. Appl. No. 12/422,031 dated Sep. 22, 2011, p. 9 Publisher: USPTO.

"Non-Final Office Action", U.S. Appl. No. 13/407,047, dated Sep. 24, 2014, 9 pp.

Wagadarikar et al., "Single disperser for coded aperture snapshot spectral imaging", "Applied Optics", dated Apr. 1, 2008, pp. B44-B51, vol. 47, No. 10, Publisher: Optical Society of America.

(56) References Cited

OTHER PUBLICATIONS

Gehm et al., "Single-shot compressive spectral imaging with a dual-disperser architecture", "Optics Express", dated Oct. 17, 2007, pp. 14013-14027, vol. 15, No. 21.
In't Zand et al., "The optimum open fraction of coded apertures. With an application to the wide field X-ray cameras of SAX", "Astronomy and Physics", dated Jan. 31, 1994, p. 665-674, vol. 288.
"Notice of Allowance and Fees Due", U.S. Appl. No. 14/350,073, dated Jan. 12, 2016, 7 pp.
"Non-Final Office Action", U.S. Appl. No. 14/350,073, dated Aug. 17, 2015, 13 pp.

* cited by examiner

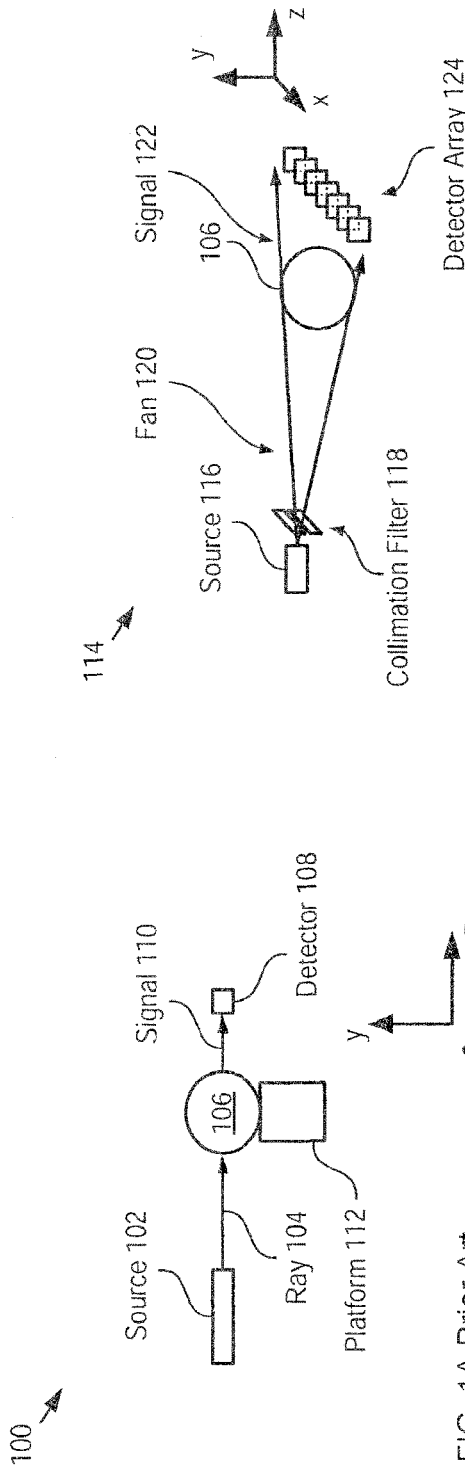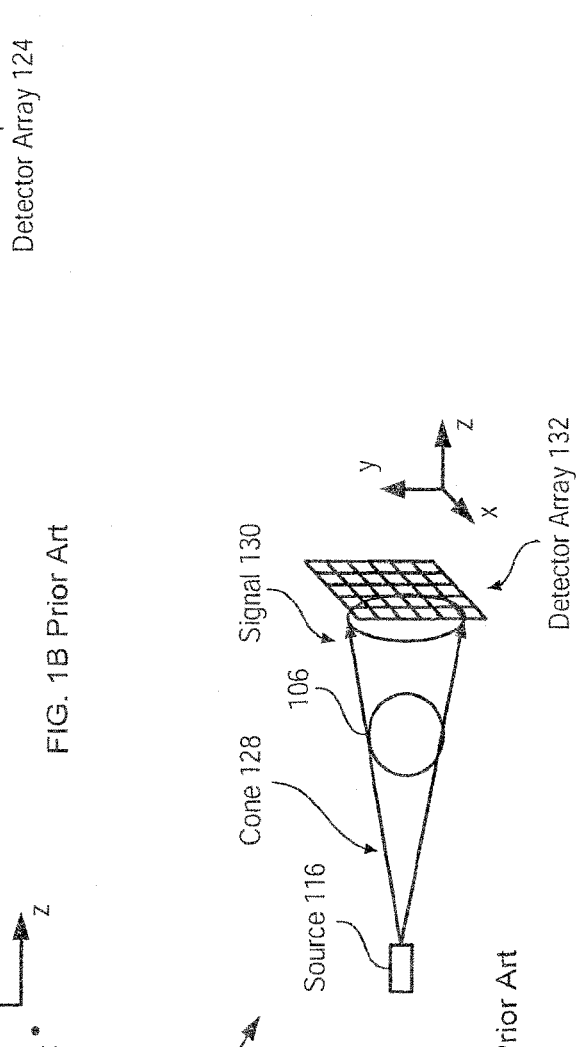
FIG. 1A Prior Art
FIG. 1B Prior Art
FIG. 1C Prior Art

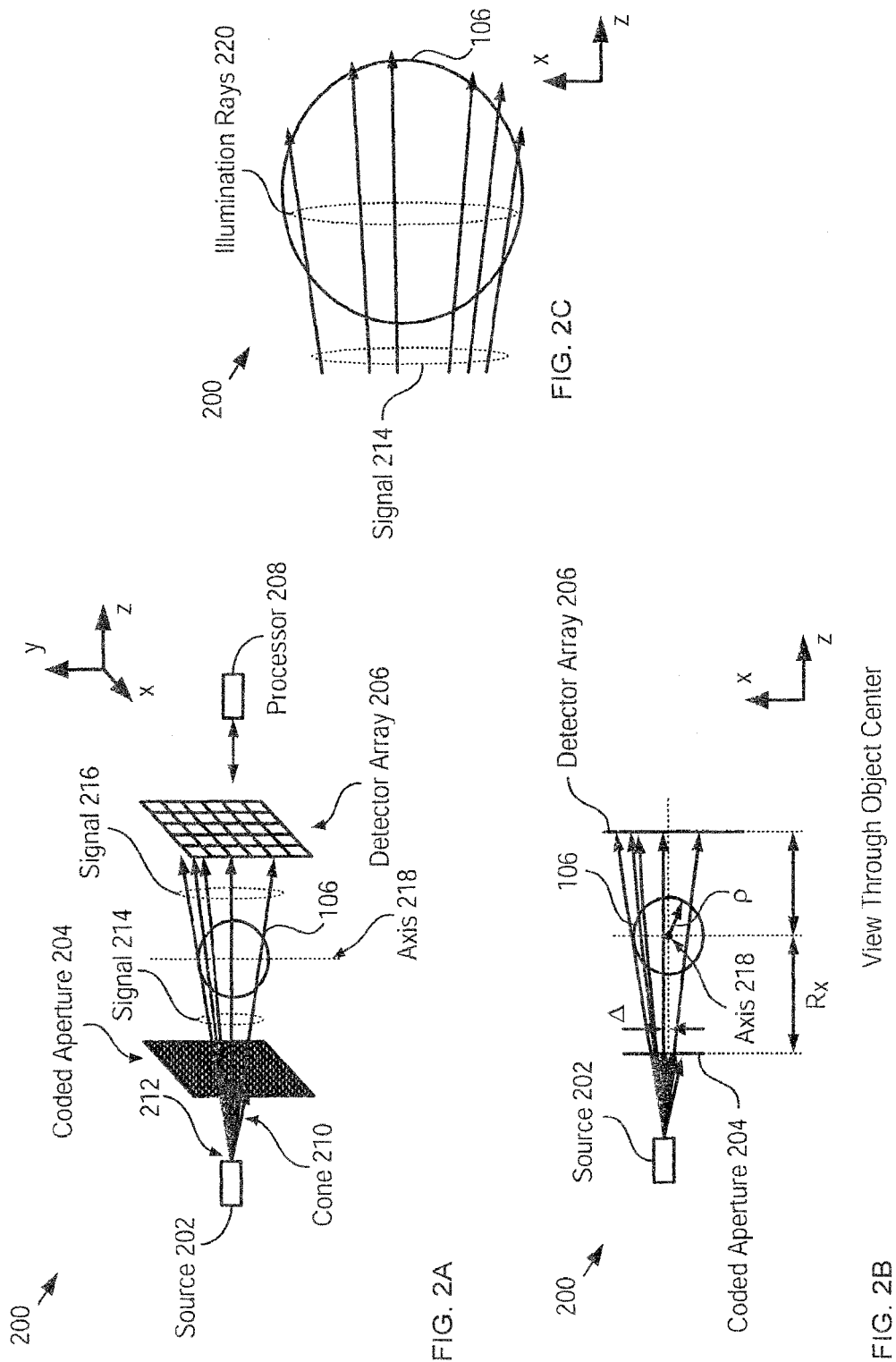

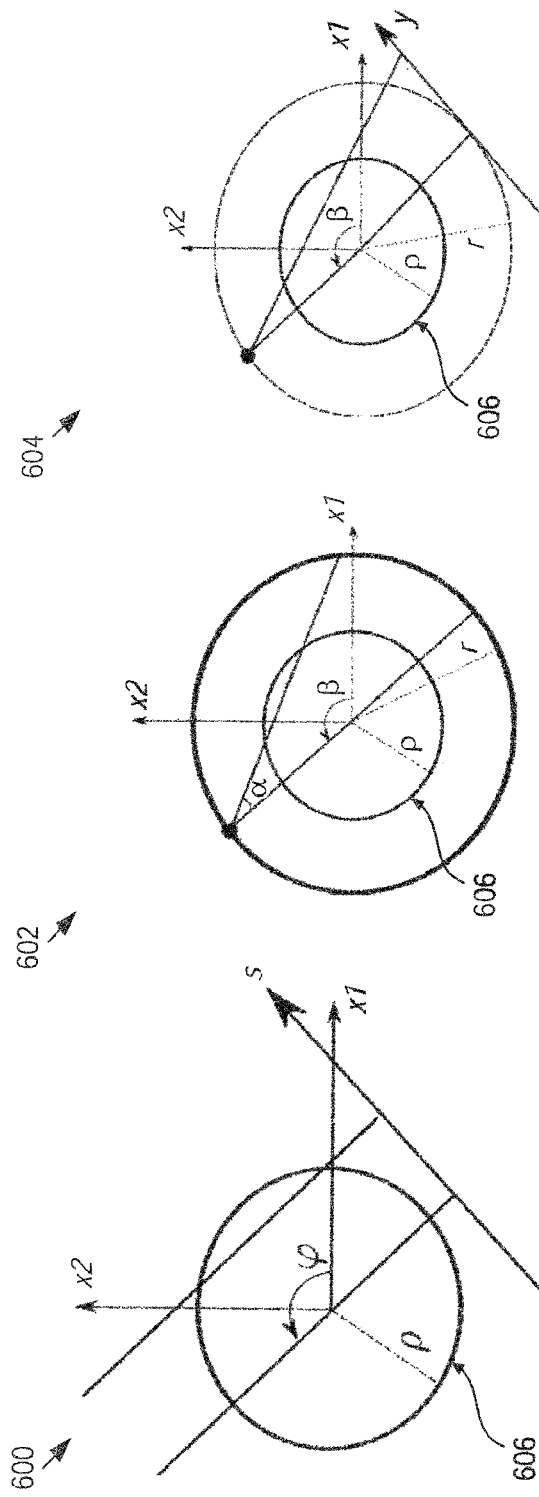

SYSTEM FOR IMPROVED COMPRESSIVE TOMOGRAPHY AND METHOD THEREFOR

FIELD OF THE INVENTION

The present invention relates to imaging in general, and, more particularly, to tomographic imaging.

BACKGROUND OF THE INVENTION

Tomographic imaging is a well-known imaging method wherein an object is interrogated by a set of illuminating rays that are transmitted through the object along a set of paths. As each ray passes through the object, it is attenuated based on the structure of the object along its respective path. The relative orientation of the object and the radiation source is repeatedly changed so that a complete data set of the attenuation characteristics of the structure of the object is obtained. Once scanning is completed, image reconstruction techniques are used to estimate the structure of the sample object from the resultant data set.

Unfortunately, an inordinate number of measurements are typically required to enable inference of the underlying structure of the object with adequate resolution. As a result, there has been a great deal of effort devoted over recent years to reducing the number of measurements required through improved sampling strategies.

Compressive sampling is one such approach. Compressive sampling is a signal processing technique for efficiently acquiring and reconstructing a signal by finding solutions to a system of linear equations that has more unknowns than equations (i.e., estimating a number of signal values from a number of measurements where the number of signal values is greater than the number of measurements). In order to find a solution to such a system, extra constraints, such as sparsity (i.e., assuming the signal contains many coefficients close to or equal to zero), are imposed on the system. Adding such a constraint allows only solutions having a small number of nonzero coefficients, which enables an entire signal to be determined from relatively few measurements.

In general, such an approach takes advantage of the redundancy in many signals. As a result, the measurements need to be maximally sensitive to as many of the basis images as possible and images that differ in a small number of basis images must be as distinguishable as possible in measurement space. The optimal measurements are, therefore, as unstructured as possible in terms of their sensitivity to basis images but should also maximally separate sparse representations in measurement space.

While compressive sampling represented a significant advance in the field of tomographic imaging, the reliance on completely random measurements that are spread out where the object is sparse suggests measuring different linear combinations of all coefficients. Unfortunately, tomographic measurements are inherently confined to a line in physical-location space. Further, most tomographic systems have the property that reducing the number of measurements implies reducing the number of angular samples or line integrals acquired, as opposed to measuring linear combinations of line integrals. This constraint, therefore, closely ties tomographic system design to classical sampling theory.

SUMMARY OF THE INVENTION

The present invention avoids some of the drawbacks of the prior art and enables imaging of an object with fewer measurements and/or at a reduced exposure level. Embodiments of the present invention are particularly well suited for use in applications such as luggage scanning, food inspection, cargo inspection, explosives detection, and medical imaging.

Embodiments of the present invention use data from a discrete, non-continuous set of illumination rays to generate a dataset from which an image of a sample object can be reconstructed. In contrast to prior-art methods, by avoiding the use of illumination rays that could provide measurable data, the present invention gives rise to one or more advantages over the prior art. These advantages include one or more of reduced illumination dosage, reduced sensor requirements, reduced system cost, improved signal-to-noise ratio, and the potential for molecular structure identification through scatter imaging.

An embodiment employs a coded aperture to modulate illumination radiation such that a sample object is interrogated with a disconnected set of illumination rays. With the source and coded aperture at a first source location, attenuation of the illumination rays is determined for a first set of paths through the object. The source and aperture are then rotated through a series of locations about the object and, at each location attenuation along a different set of paths through the object is determined. A multidimensional image of the object is reconstructed from the generated data set using compressive sampling techniques.

In some embodiments, the same coded aperture is used at each source location. In some embodiments, a different coded aperture is used at each source location. In some other embodiments, a coded aperture selected from a set of coded apertures is used at each location, where the set includes fewer members than the number of source locations. In some embodiments, a coded illumination sequence is used to modulate the illumination rays at one or more of the source locations.

In some embodiments, the illumination radiation is not modulated and the object is interrogated with a continuous set of illumination rays. A sparse set of detectors is then used to subsample the illumination rays after they have passed through the object.

In some embodiments, a coded aperture is used to mask the illumination rays after they have exited the object so as to enable scatter imaging of the object. In some of these embodiments, the scatter image data is analyzed to enable identification of one or more material constituents of the object.

An embodiment of the present invention is a method for imaging an object, wherein the method comprises: detecting a set of illumination rays, wherein the set includes illumination rays that are discrete and non-continuous; generating a dataset that includes values for the attenuation of each illumination ray of the set thereof, the attenuation being based on the structure of the object along the path of the illumination ray; and reconstructing an image of the object based on the dataset.

BRIEF DESCRIPTION OF THE DRAWINGS

FIGS. 1A-C depict exemplary prior-art projection tomography systems.

FIGS. 2A-C depict schematic drawings of different views of a filtered-illumination tomographic imaging system in accordance with a first embodiment of the present invention.

FIGS. 6A-C depict different scanning two-dimensional scanning strategies and their corresponding parameters for line integrals.

DETAILED DESCRIPTION

Figure 3:
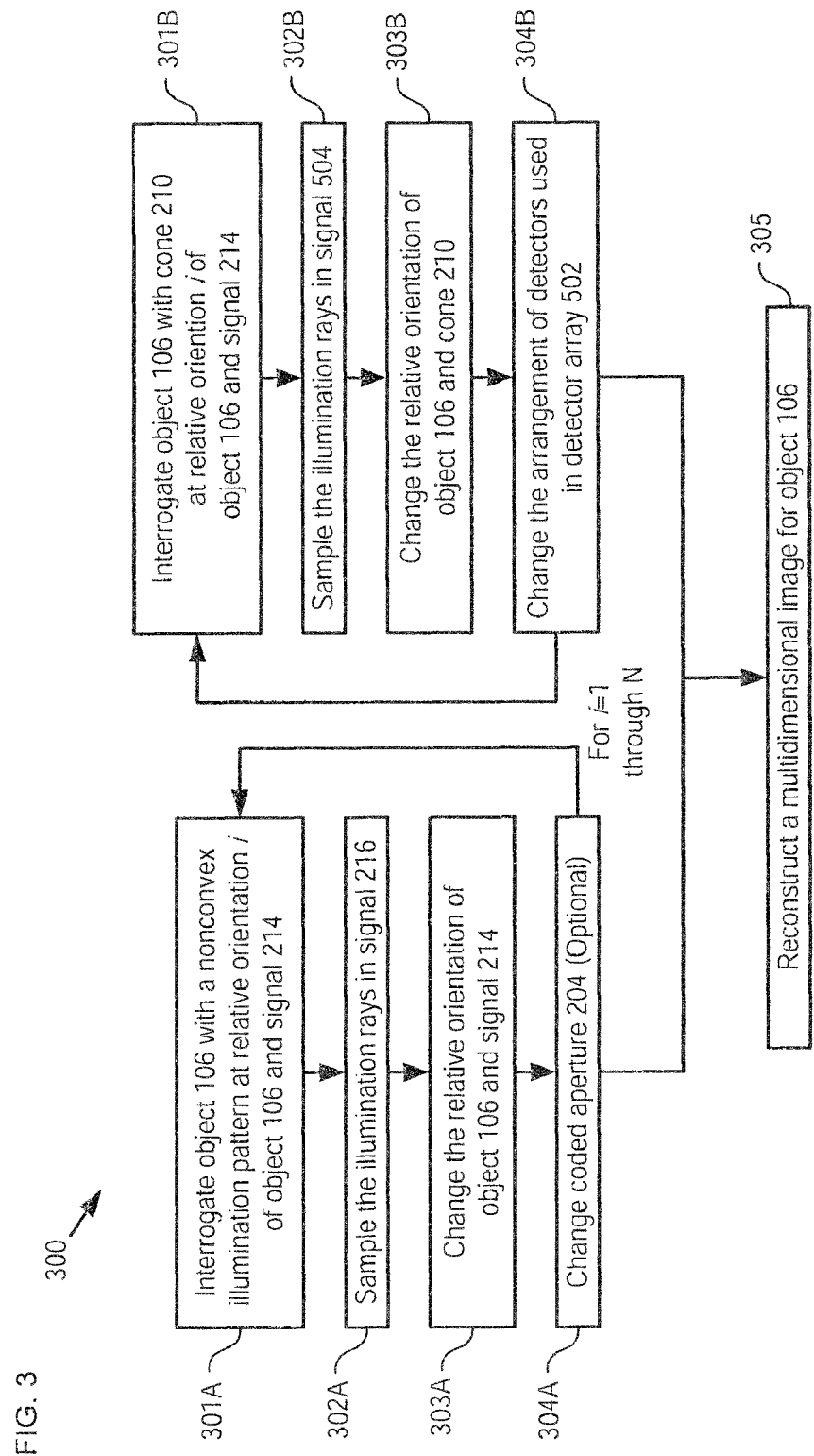
FIG. 3 depicts two sub-methods suitable for imaging an object in accordance with the present invention.

In prior-art tomographic imaging systems, an object is interrogated with either a pencil beam, or a continuous set of illumination rays that is provided in the form of either a "fan" beam, or a "cone" beam. A pencil beam uses only one illumination ray, whereas cone beams and fan beams include sets of rays all arising from the same vertex and are substantially confined to either a cone or a 2-dimensional cross-section of a cone, respectively.

FIGS. 1A-C depict exemplary prior-art projection tomography systems.

System 100 is exemplary of a prior-art, one-dimensional tomographic-imaging system. In system 100, source 102 is a collimated source that it emits ray 104 as a narrow "pencil" beam of illuminating radiation. Ray 104 passes through object 106 and is detected at detector 108 as signal 110.

The structure of object 106 along the path of ray 104 gives rise to attenuation as the radiation traverses the object. Representing object density as f(x), signal 110 is given by:

$$g = I_o e^{-\int f(x)dx}, \quad (1)$$

where the integral is over the line ray 104 follows through object 106. Taking the logarithm of equation (1) to isolate the line integrals gives:

$$-\int_{ray} f(x)dx, \quad (2)$$

where line integrals through f(x) are the basic measurable of system 100. Measurement and coding strategy typically includes selecting a subset of these integrals to measure, determining the order in which they are measured, and deciding whether to measure them individually or in groups.

System 114 is exemplary of a prior-art, two-dimensional tomographic-imaging system. In system 114, source 116 emits radiation that passes through collimation filter 118 and emerges as "fan" 120. Fan 120 includes illumination rays that are substantially confined to a plane. After passing through object 106, the now-attenuated illumination rays collectively define signal 122, which is detected at detector array 124.

System 126 is exemplary of a prior-art, three-dimensional tomographic-imaging system. In system 126, the output of source 116 emerges as a "cone" of illuminating radiation (i.e., cone 128) comprising illumination rays that propagate from a common vertex located at the output of source 116. These illumination rays pass through object 106 to collectively define signal 130, which is detected at detector array 132.

Like signal 110, each illumination ray in signals 122 and 130 is described by equations (1) and (2) above.

In each of systems 100, 114, and 126, object 106 is mounted on platform 112, which can translate and rotate object along and about each of the x-, y-, and z-axes. In some cases, object 106 remains stationary while the source/detection system is rotated and/or translated about it. Relative motion of the object and scanning system enables the imaging systems to obtain a data set sufficient to detect object features with reasonable resolution and/or reconstruct a multidimensional image of the object.

It should be noted that in each of systems 100, 114, and 126, as well as conventional tomographic imaging systems in general, the set of ray projections obtained is measured using "continuous" illumination patterns and continuous scanning or rotation. For the purposes of this Specification, as well as the appended claims, a "continuous illumination pattern" is defined as a range of illumination rays that is smoothly connected without gaps, such as in a fan or cone. In other words, a continuous illumination pattern includes a set of rays that collectively form a continuous pattern along at least one dimension.

Unfortunately, interrogating a sample object with a continuous illumination pattern can have several drawbacks. First, while many transmitted photons travel along the desired path directly from source to detector, some photons on each path can scatter from within the object via various physical mechanisms, such as Compton and coherent scatter. These scattered photons can reach any of the detectors by passing through a non-direct trajectory becoming a significant source of noise. By interrogating the sample object with a continuous beam of radiation, the noise level due to scatter is increased, reducing the signal-to-noise ratio (SNR) of the imaging system and degrading image resolution.

In addition, in some cases, it is desirable to detect scattered radiation as it can provide useful information about the molecular structure of the sample object. Unfortunately, for continuous illumination patterns, discriminating scatter radiation from projected rays is extremely difficult, if not impossible.

Further, in many applications, such as medical imaging, it is desirable to limit the total radiation dose to which a patient is subjected. Using a continuous illumination beam, options for reducing total radiation exposure are limited to reducing the power level of the source, reducing exposure time, or scanning the object at fewer source/object orientations. Unfortunately, these approaches can degrade SNR and/or image quality.

It is an aspect of the present invention that data from a discontinuous set of illumination rays, or sub-sampling a continuous set of illumination rays can yield at least comparable image quality to prior-art imaging methods with fewer measurements, while affording embodiments of the invention with advantages including:
  i. reduced dosage level; or
  ii. molecular structure analysis via detection of scatter radiation; or
  iii. improved SNR; or
  iv. any combination of i, ii, and iii.

It is an aspect of the present invention that these benefits can be derived by sampling illumination rays projected through an object, where the illumination rays are sampled at a sampling rate that is lower than dictated by classical sampling theory. Embodiments of the present invention accomplish this via one of two broad approaches: (1) filtered illumination, wherein an object is interrogated via an illumination pattern that is defined by a set of discrete, non-continuous illumination rays; and (2) detector subsampling, wherein a continuous illumination pattern is used to interrogate an object but only some of the illumination rays in the pattern are sampled at a detector array that is sparser than anticipated by classical sampling theory. For the purposes of this Specification, as well as the appended claims, a "non-continuous illumination pattern" is defined as a range of discrete illumination rays that is discontinuous. In other words, the pattern includes a set of discrete illumination rays that are not smoothly connected. It should be noted that a non-continuous illumination pattern can include some rays that collectively form a subset of illumination rays that are continuous.

Filtered Illumination

FIGS. 2A-C depict schematic drawings of different views of a filtered-illumination tomographic imaging system in accordance with a first embodiment of the present invention. System 200 includes source 202, coded aperture 204, detector array 206, and processor 208. System 200 is representative of a class of systems suitable for interrogating an object using filtered illumination. FIGS. 2A and 2B depict perspective and top views, respectively, of system 200. FIG. 2C depicts an expanded view of illumination rays 220 as they traverse object 106 in system 200.

FIG. 3 depicts two sub-methods suitable for imaging an object in accordance with the present invention. Sub-method 300A begins with operation 301A, wherein object 106 is interrogated with a non-continuous illumination pattern at a first source location. For the purposes of this Specification, including the appended claims, the term "source location" is defined to mean an orientation between source, object, and detector array. In some embodiments, a different source location is attained by rotating and/or translating the source and detector array about the object while the object remains substantially fixed. In some embodiments, the source location is changed by rotating and/or translating the object while the source and detector array remain fixed. Further, it should be noted that the terms "source position" and "view-angle" are considered synonymous in the art and are used interchangeably herein.

Source 202 provides a cone-shaped beam of radiation (i.e., cone 208) suitable for interrogating object 106. The radiation in cone 210 propagates along the z-direction from vertex 212, as shown.

Coded aperture 204 is a spatial filter that modulates the radiation in cone 210 by blocking some illumination rays in the cone but allowing other rays to pass through. As a result, coded aperture 204 gives rise to a non-continuous illumination pattern that defines signal 214, which is provided to object 106.

Figure 4:
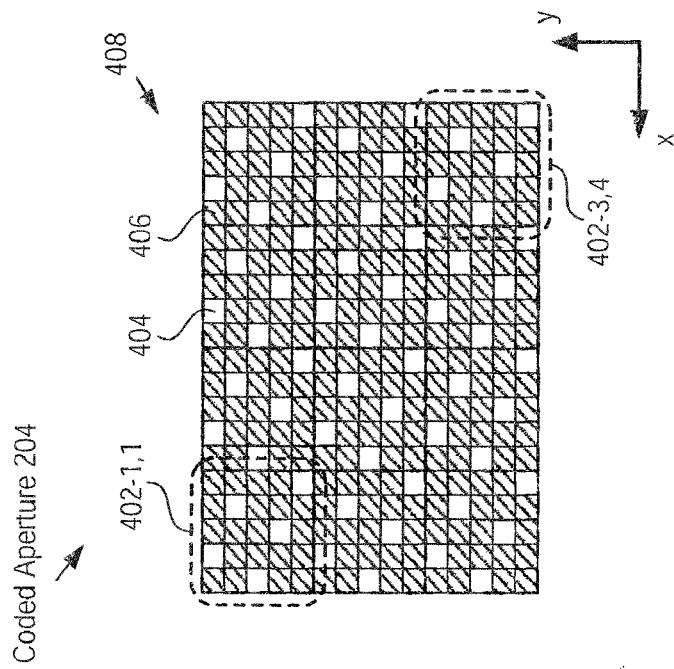
FIG. 4 depicts a schematic drawing of a portion of a coded aperture in accordance with the first embodiment of the present invention.

FIG. 4 depicts a schematic drawing of a portion of a coded aperture in accordance with the first embodiment of the present invention. Coded aperture 204 includes a two-dimensional array of fields 402.

Each of fields 402 includes regular two-dimensional array of equal size regions. In the first embodiment, each of fields 402 comprises 5 rows of regions and 5 columns of regions. Each row comprises one transmissive region 404 and 4 non-transmissive regions 406. The regions of field 402 within each field 402 are arranged such that no two transmissive regions 404 are contiguous within the field. Further, the plurality of fields 402 within coded aperture 204 is arranged such that no two transmissive regions 404 are contiguous within coded aperture 204.

One skilled in the art will recognize that the number and arrangement of fields 402 in coded aperture 204, as well as the number, arrangement, size and shape of each of the regions that compose the fields of coded aperture 204 is design dependent and/or application dependent. Although regions 404 and 406 are depicted as being square, one skilled in the art will recognize, after reading this disclosure, that any suitable shape can be used for these regions.

As each of illumination rays 220 transits object 106, it is attenuated based on the structure of the object along its path. The attenuated illumination rays exit object 106 as signal 216.

At operation 302A, the illumination rays in signal 216 are sampled at detector array 206 and their intensities are provided to processor 208. Processor 208 determines an attenuation level for each illumination ray and adds them to a data set for object 106.

Prevailing opinion in the field of tomographic imaging would suggest that measurement of complete fan or cone data is more optimal than sequential or parallel measurement of discrete ray projections more sparsely distributed over the range of possible projections. As demonstrated in FIG. 8 below, however, embodiments of the present invention provide performance in contrast to this expectation.

It is an aspect of the present invention that, although seemingly counterintuitive, blocking illumination rays (or not detecting illumination rays) that would otherwise provide measurable data yields substantial advantages in reducing illumination dosage, reducing sensor requirements, and/or enabling scatter measurement in an imaging system.

At operation 303A, source 202, coded aperture 204, and detector array 206 are rotated about at least one of axis 218 and/or translated along the y-direction to another of N source locations and operations 301A and 302A are repeated. In the first embodiment, the N source locations are pre-determined and uniformly positioned about object 106. In some embodiments, the N source locations are randomly selected about object 106.

At optional operation 304A, the pattern code of coded aperture 204 is changed so that signal 214 includes a different non-continuous illumination pattern. In some embodiments, a different coded aperture is used at each source location. In some embodiments, the coded aperture used at each source location is selected from a set of coded apertures, which typically has fewer members than N. As a result, each coded aperture is used at several different source locations.

In some embodiments, the pattern code for the coded aperture used at a source location is determined based on previously taken measurements and on which next measurement is most informative of the object. As a result, illumination rays can be proactively directed to object regions where they are most useful, thereby avoiding exposure of an object to unnecessary dosage in the other object regions.

By varying the structure of coded aperture 204 at different source locations, and/or the positions of source 202 and coded aperture 204 relative to object 106, it is possible to acquire complete projection data over time.

The present invention enables automatic determination as to whether enough information about the object has been acquired. In embodiments, adaptive selection is used to select the designs of each of a set of coded apertures. At least two ways for performing adaptive selection are contemplated within scope of the present invention: (1) a set of differently coded apertures is designed based on a series of measurements of a physical phantom for a specific task (e.g., a head CT scan, mammography, etc.); and (2) the choice for the best coded aperture for the next measurement is made from the available set of coded apertures developed in (1).

A general framework for experimental design is based on a Bayesian framework for compressive sensing, wherein object 106 is described using a statistical model. As a result, in addition to expected values that represent the most likely estimate, error-bars are also available. This framework enables uncertainty to be modeled, which enables an intelligent choice between different possible measurements according to a degree of confidence in their outcomes. In other words, the mutual information between the object and the next measurement is used as selection criteria. Further, the error-bars can be used as indication of the confidence in the object reconstruction and therefore as a stopping criterion.

In (1), a complete measurement of a physical phantom for a specific task is first taken. Then, a computational process is used to select the rays that are most informative for each measurement. The selected rays dictate the aperture codes that can be manufactured and used for the actual measurements.

In (2), the best coded aperture for the next measurement is selected out of the available set of apertures designed in the first method. The possible measurements are numerically scored according to the mutual information criterion and the measurement having the highest score is performed. In all cases, once a measurement is taken, the object estimate and its error-bars are updated and the process is repeated until the error-bars decrease to a prescribed level.

The present invention enables reconstruction of an image using a dataset derived from non-continuous patterns of illumination rays. The system and method described thus far develop such a dataset by interrogating an object with a non-continuous set of discrete illumination rays. As mentioned briefly above, however, an alternative approach within the scope of the present invention is to interrogate the object with a continuous set of illumination rays and subsample the illumination rays at a sparse detector array after they have passed through the object.

Detector Subsampling

Figure 5:
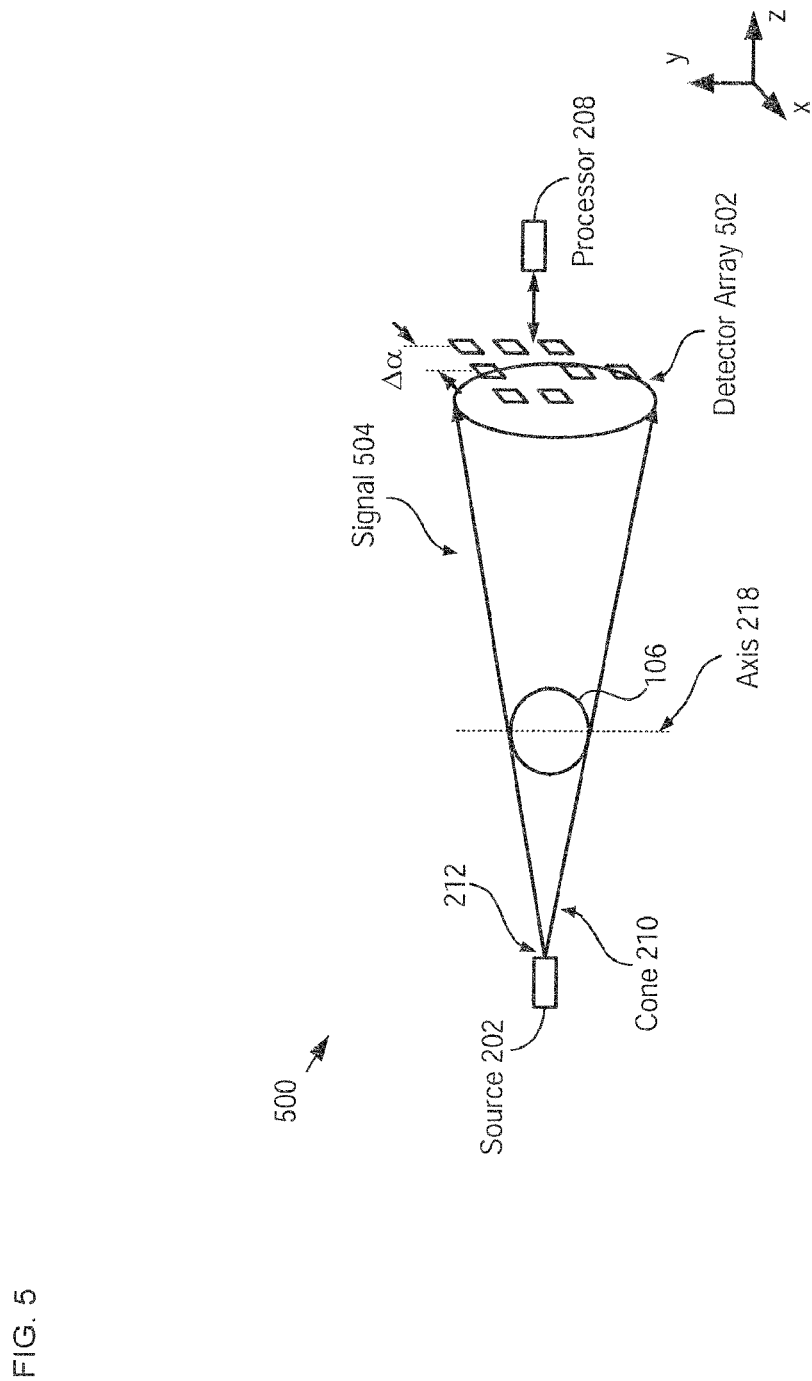
FIG. 5 depicts a schematic drawing of a perspective view of a detector-subsampled tomographic imaging system in accordance with a second embodiment of the present invention.
Figure 7B:
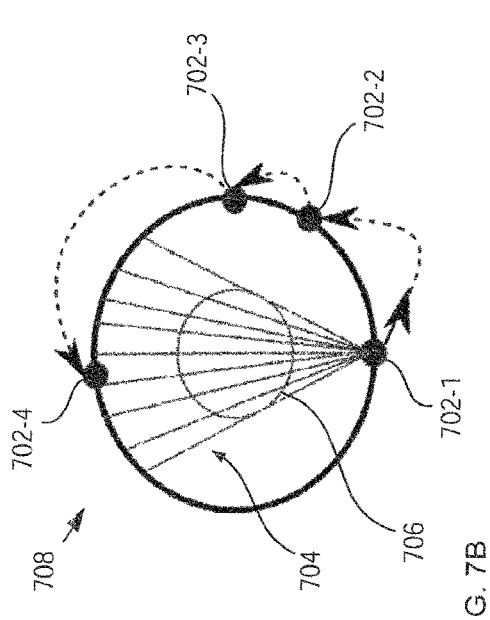
FIGS. 7A-D depict schematic drawings of four basic sampling strategies.
Figure 7D:
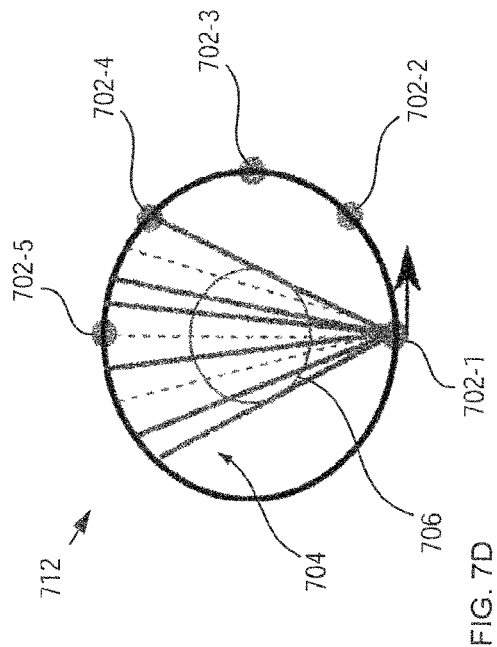
Figure 7A:
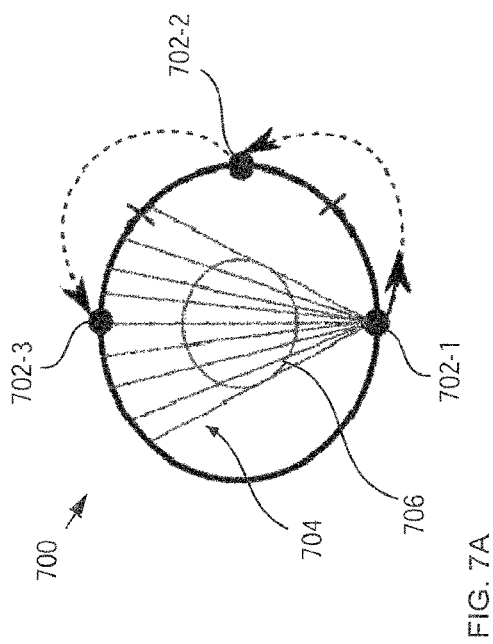
Figure 7C:
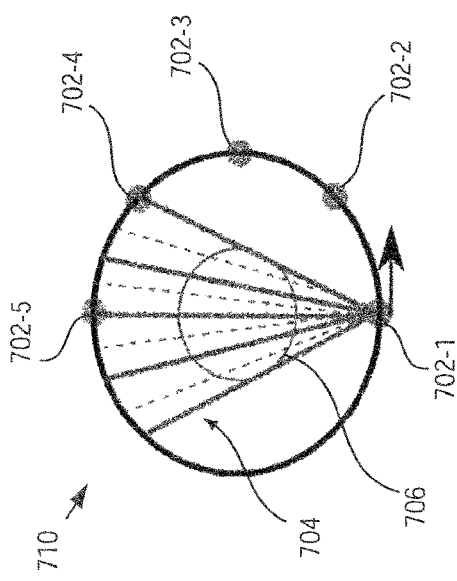

FIG. 5 depicts a schematic drawing of a perspective view of a detector-subsampled tomographic imaging system in accordance with a second embodiment of the present invention. System 500 includes source 202, detector array 502, and processor 208.

Sub-method 300B begins with operation 301B, wherein object 106 is interrogated with a continuous illumination pattern at a first source location.

It should be noted that system 500 does not include a coded aperture between the source and the object. As a result, object 106 is interrogated with the full set of illumination rays in cone 210 (i.e., with a continuous illumination pattern).

In order to further the understanding of the present invention, a discussion of the theory of sampling strategies upon which some embodiments of the present invention are based is presented here.

As would be understood by one skilled in the art, a horizontal slice taken through cone 210 is analogous to a fan-shaped beam. For the purposes of this treatment of sampling strategies, the discussion herein is limited to consideration of source locations in a plane in which a fan shaped beam is used to interrogate object 106.

In a 2D sampling function, denoted f(x), with $x=(x_1,x_2)$, measured line integrals are arranged in a pattern referred to herein as a scanning geometry or, more simply, geometry.

FIGS. 6A-C depict different scanning two-dimensional scanning strategies and their corresponding parameters for line integrals.

In each of diagrams 600, 602, and 604, disc 606 denotes the image domain for object 106, where the function f is to be reconstructed from measurements of the line integrals. Disc 606 has a radius, r.

Diagram 600 shows that in the translate-rotate geometry, the lines come in parallel bundles and are parameterized by the direction of the beam, defined by angle φ, and the displacement, s, perpendicular to the central ray in a bundle. The measurements in this configuration correspond to samples of the conventional Radon transform defined by:

$$Rf(\varphi,s)=\int_{x\cdot\theta=s}f(x)dx, \theta=(\cos\varphi, \sin\varphi). \quad (3)$$

A commonly used physical configuration is the fan-beam geometry, with lines arranged into fans emanating from focal points (point sources) distributed over a circle around the origin; these are parameterized by the angular location of the source, β, and the angle, α, between each ray and the "central ray" that goes through the origin, as shown in diagram 602. This gives rise to the fan beam transform D, defined by:

$$Df(\beta,\alpha)=\int_{L(\beta,\alpha)}f(x)dx, \quad (4)$$

where L(β,α) is the line connecting the source and detector. The relation to the Radon transform is given by:

$$Df(\ominus,\alpha)=Rf(\beta+\alpha-\pi/2, r\sin\alpha), \quad (5)$$

where r is the distance of the source from the origin. An alternative configuration is shown in diagram 604, where a linear displacement is used for detectors instead of angle, α.

It should be noted that in real physical configurations only a discrete set of parameter values can be measured. Although in the continuous case the fan-beam transform is a re-parameterization of the Radon transform, in the discrete case, the grids of these two geometries will be different. For example, trying to reorder fan-beam measurements with only a few view angles into parallel lines will result in many missing detector and view angle samples in the parallel-beam geometry.

Results obtained from each of a filtered-illumination approach and detector-subsampled approaches are compared below, where the variable that is not being under-sampled is set to the minimal required resolution according to classical sampling theory.

FIGS. 7A-D depict schematic drawings of four basic sampling strategies.

Diagram 700 shows an example of uniform-view-angle (UV) subsampling, which is known in the prior art. For clarity, diagrams 700, 708, 710, and 712 show illumination rays for only one source position 702.

In UV subsampling, source locations 702-1 through 702-N (N=3, as shown) are distributed uniformly about imaged domain 706, which corresponds to object 106. In addition, no coded aperture is used to create discrete illumination rays. As a result, a complete set of detectors is used to detect substantially all illumination rays 704 in the signal used to interrogate object 106.

Diagram 708 shows an example of random-view-angle (RV) subsampling, which is also known in the prior art.

In RV subsampling, source locations 702-1 through 702-N (N=4, as shown) are selected randomly about imaged domain 706. As in UV subsampling, no coded aperture is used to create discrete illumination rays. As a result, a complete set of detectors is used to detect substantially all illumination rays 704 in the signal used to interrogate object 106.

Diagram 710 shows an example of Uniform-Detector (UD) subsampling in accordance with the present invention. In diagram 710 (as well as diagram 712), measured line integrals are shown as solid lines, while non-measured line integrals are shown as dashed lines. In UD subsampling, either: (1) a coded aperture is used at each source location to modulate the radiation signal used to interrogate object 106 (as in system 200); or detector array having a sparse array of detectors is used at each location to detect a subset of illumination rays from a continuous illumination pattern that is used to interrogate the object (as in system 500). As a result, a subset of illumination rays are detected at detectors whose locations selected uniformly (e.g., by using only every other detector in a uniformly-spaced detector array) based on the code employed at the coded aperture. Also, in UD subsampling, a complete set of source locations is used.

Diagram 712 shows an example of Random-detector (RD) subsampling in accordance with the present invention. In RD subsampling, either: (1) a different coded aperture is used at each source location to modulate the radiation signal used to interrogate object 106 (as in system 200); or (2) a different detector array arrangement is used at each source location to detect a different subset of illumination rays from a continuous illumination pattern used to interrogate the object (as in system 500). As a result, a subset of illumination rays are detected at detectors whose locations are selected randomly while a complete set of source locations is used.

In order to demonstrate the advantages afforded embodiments of the present invention, RD subsampling is compared here to cases where both view and detector sampling is done according to the minimal resolutions dictated by classical sampling theory (referred to as "complete measurements"). Further, three variations of RD subsampling are also considered here, namely:
  i. Dynamic-Random-Detector (RD) subsampling, wherein detectors are selected randomly per source location with a different code used at each source location;
  ii. Semi-Dynamic-Random-Detector (SDRD) subsampling, wherein the set of codes has fewer members than the number of source locations;
  iii. Static-Random-Detector (SRD) subsampling, wherein the same code is used at all source locations.

Sampling theory for tomography originated from classical sampling theory, which permits the reconstruction of a band-limited function from its values on a regular grid or lattice. However, the imaged domain is always of finite support and strictly speaking there are no band-limited functions of compact support. Therefore a widely used approach is to consider essentially band limited functions instead (i.e., the frequency content outside some frequency band is considered negligible). Given a desired resolution of some size, sampling conditions are derived for stable reconstruction of details up to that size. Here, "stable" is defined to mean that small error in measurements does not result in arbitrary large error in the reconstructed function.

As shown in FIG. 6B, object 106 is contained inside a disk of radius ρ outside which the object does not exist. Sufficient sampling conditions for several different 2D geometries are summarized in Table 1 below for reconstructing image details of up to size δ. There are two different resolutions that are required according to this theory, one for the source location intervals and one for detector intervals.

TABLE 1

Sufficient sampling conditions for reconstructing details of up to size d for scanning geometries

| Geometry | View Interval | Detector Interval |
|---|---|---|
| Parellel | $\Delta\varphi = \dfrac{\delta}{2\rho}$ | $\Delta s = \dfrac{\delta}{2}$ |
| Fan-Curved Detector | $\Delta\beta = \dfrac{r+\rho}{r}\dfrac{\delta}{2\rho}$ | $\Delta\alpha = \dfrac{\delta}{2r}$ |
| Fan-Flat Detector | $\Delta\beta = \dfrac{\delta}{2\rho}\dfrac{r+\beta}{r}\left(1-\dfrac{\rho^2}{r^2}\right)$ | $\Delta y = \dfrac{\delta}{2}$ |

Returning now to FIG. 5, at operation 302B, the illumination rays in cone 210 are subsampled at detector array 502 after they have traversed object 106.

Detector array 502 includes a sparse arrangement of detectors. For the purposes of this Specification, including the appended claims, a "sparse arrangement of detectors" is defined as an arrangement of detectors wherein at least some of the detectors are spaced at an interval that is greater than as dictated by classical sampling theory, as indicated in Table 1. As a result, detector array 502 includes fewer detectors than would be used in the prior art.

At operation 303B, source 202, coded aperture 204, and detector array 206 are rotated about at least one of axis 218 and/or translated along the y-direction to another of N source locations and operations 301A and 302A are repeated. In the first embodiment, the N source locations are pre-determined and uniformly positioned about object 106. In some embodiments, the N source locations are randomly selected about object 106.

At optional operation 304B, the arrangement of detectors used in detector array 502 is changed so that a different non-continuous illumination pattern is sampled after it has traversed object 106. In some embodiments, a different detector arrangement is used at each source location. In some embodiments, the detector arrangement used at each source location is selected from a set of detector arrangements, which typically has fewer members than N. As a result, each detector arrangement is used at several different source locations.

Once a dataset of attenuation values has been developed, by either interrogating object 106 with a non-continuous pattern of illumination rays or by subsampling a continuous set of illumination rays after they have passed through the object, an image can be reconstructed based on this dataset.

At operation 305, which is common to both of sub-methods 300A and 300B, processor 210 reconstructs a multidimensional image for object 106 based on line integrals through the object, as described above and with respect to FIGS. 1A-C.

In some embodiments, the reconstruction performed in operation 305 assumes that the mean number of photons reaching a detector after a ray has passed through the object can be given by Beer's law as:

$$I_i = I_{i0}\exp(-\int_{L_i} f(x)dz)), \quad (6)$$

where i denotes a source-detector pair connected by ray $L_i$, $L_{i0}$ is the mean number of photons that would reach the ith detector without the object, and f≥0 is the distribution of the linear attenuation constant in mm$^{-1}$ inside the object under test. Denoting $d_i$ and $d_{i0}$ as the ith detector reading with/without the object, we define the log transformed and calibrated measurements as $$y_i = \ln \frac{d_{i0}}{d_i} = \ln d_{i0} - \ln d_i. \tag{7}$$

For a monoenergetic source, the detected signal $d_i$ is generally assumed to be Poisson distributed with mean and variance equal to $I_i$ given by equation (6) above. For large values of $I_i$, the log transformed measurement $y_i$ can be shown to have a Gaussian distribution.

After discretizing the line integrals and f (where f is described by y=Hf, where $f \in \mathbb{R}_+^M$ represents the object of interest discretized using a 2D Cartesian grid (image) and rearranged as a vector, f is the attenuation of x-rays per unit length inside object 106, in unites mm−1, and $H \in \mathbb{R}_+^{N \times M}$ contains the intersection length of each ray with each pixel inside the image in unties of mm, with row index corresponding to line integral and column index corresponding to image pixel), the Gaussian noise model reads $$y \sim Hf + \epsilon, \quad \epsilon \sim \mathcal{N}(0, \Sigma), \tag{8}$$

where the ith element in y is given by equation (7) above and ε is a normally distributed noise with zero mean and covariance matrix given by:

$$\Sigma = \text{diag}[I_0^{-1} \exp(Hf)]. \tag{9}$$

The reconstruction algorithm employed here is the relevance vector machine (RVM) which was first introduced in the prior art in the context of machine learning and later adopted for compressive sensing. In the RVM, the inversion of compressive measurements is done from a Bayesian perspective. Specifically, if f is anticipated to be sparse in some basis (i.e., in the representation f=Ψx) many x have small values. This belief is represented by a probability density function for the weights x that assigns high probability to small weights but still allows a few large weights. Instead of just providing a single estimate for x, a full posterior probability distribution function is computed using Baye's rule. The posterior distribution represents the current state of knowledge, combing the prior knowledge with the information gained by measurements, and describes how likely different possible estimates for x are. Typical choices for point estimates are the mean of the posterior distribution for x or the value of x for which the posterior is maximal (maximum a posteriori=MAP). In addition to a point estimate for x, the Bayesian approach also provides error bars that can be used to give a sense of confidence in the estimated value. These error bars can also be used to guide the optimal design of additional CS measurements, implemented with the goal of reducing uncertainty of x or f. It should be noted that the RVM performs a non-linear reconstruction of the object by imposing a sparse solution and, therefore, utilizes the underlying signal model.

In operation 305, a simple version of RVM is employed, with some minor modifications to adapt it to transmission tomography. The noise covariance matrix is presumed as $\Sigma = \sigma^2 I$ with I being the identity matrix. In order to use the standard model in the RVM algorithm, two modifications must be performed. The object-dependent covariance matrix is estimated by replacing Hf with the measurements y. In addition, a noise whitening procedure must be applied by replacing y and H with $\tilde{y} = \Sigma^{-1/2} y$ and $\hat{H} = \Sigma^{-1/2} H$, respectively, reducing the covariance matrix for $\tilde{y}$ to the identity matrix.

Figure 8:
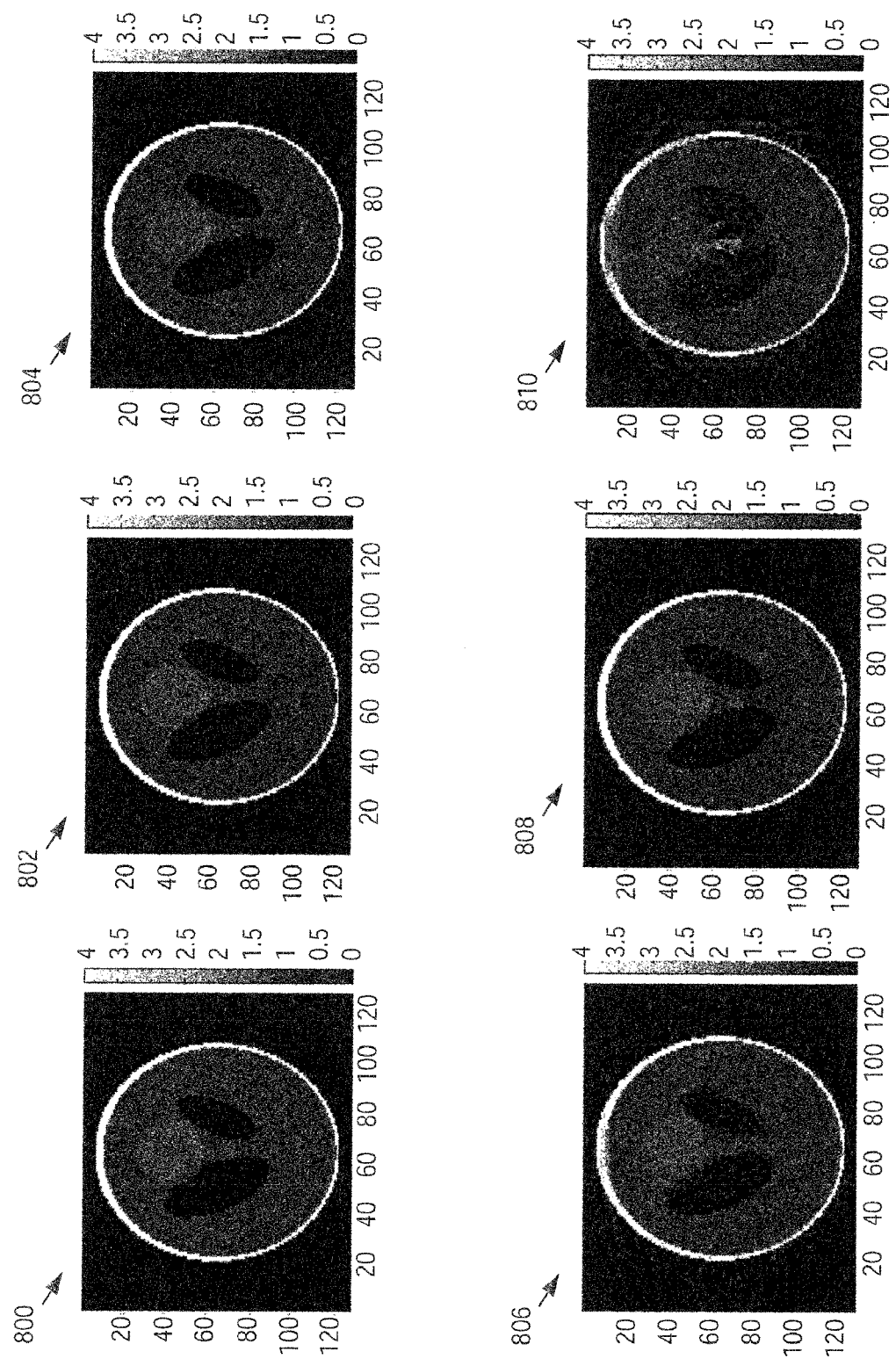
FIG. 8 depicts reconstructed images, based on simulated data, using nonlinear compressed-sensing reconstruction methods (RVM method) that make use of the natural sparsity of the object in the wavelet representation.

FIG. 8 depicts reconstructed images, based on simulated data, using nonlinear compressed-sensing reconstruction methods (RVM method) that make use of the natural sparsity of the object in the wavelet representation. In all cases, only four iterations of RVM have been used. The data is generated according to the model in equations (8) and (9) above with $I_0 = 10^5$.

Plot 800 is the synthetic object that was used to generate the simulations (referred in the art as "the truth").

Plot 802 is a reconstruction based on a full set of illumination rays through the object. Plot 802 is virtually indistinguishable from plot 800.

Plot 804 is a reconstruction based on dynamic random detector (DRD) sampling of the object. It can be seen that the image quality in plot 804 is not significantly degraded from that of pot 802.

Plot 806 is a reconstruction based on random view (RV) sampling of the object.

Plot 808 is a reconstruction based on semi-dynamic random detector (SDRD) sampling of the object, wherein ten masks are used. SDRD sampling gives rise to image quality comparable to that of each of plots 804 and 802.

Plot 810 is a reconstruction based on static random detector (SRD) sampling of the object using a single mask. Some degradation of image quality is evident from plot 810.

Each of plots 804, 806, 808, and 810 is a reconstructed image for a random undersampling x32, where values represent the attenuation per unit length divided by the attenuation per unit length of water.

Figure 9:
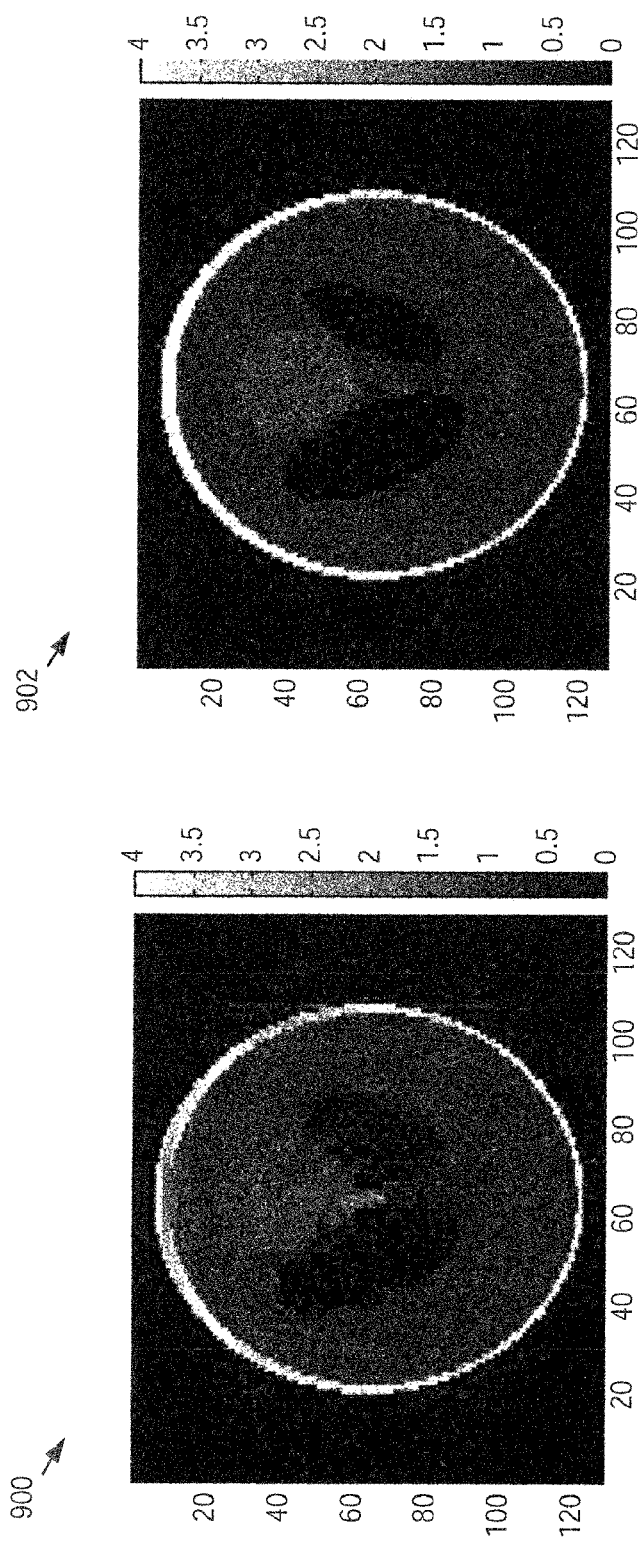
FIG. 9 depicts reconstructed images, based on simulated data, using nonlinear compressed-sensing reconstruction methods (RVM method) that make use of the natural sparsity of the object in the wavelet representation.

FIG. 9 depicts reconstructed images, based on simulated data, using nonlinear compressed-sensing reconstruction methods (RVM method) that make use of the natural sparsity of the object in the wavelet representation. Images 900 through 904 are reconstructions for uniform undersampling x32. In all cases, only four iterations of RVM have been used. The data is generated according to the model in equations (8) and (9) above with $I_0 = 10^5$.

Image 900 is a reconstructed image for Uniform Detector (UD) sampling.

Image 902 is a reconstructed image for Uniform View (UV) subsampling.

A comparison of images 900 and 804 show that, contrary to prevailing wisdom, the random detector (RD) approach yields significantly improved results.

Based on the results provided herein, it can be seen that the present invention enables embodiments having significant advantages over tomographic imaging systems of the prior art. As discussed above, these advantages include:
  i. reduced illumination dosage; or
  ii. lower cost due to a need for fewer detectors; or
  iii. measurement of projections to an optimized sequence; or
  iv. any combination of i, ii, iii, and iv.

It is yet another aspect of the present invention that information theoretic measures may be used to choose a mathematically optimal measurement strategy that selects rays to be measured in parallel groups or in sequences that can substantially optimize system performance.

There are numerous motivations for reducing the number of tomographic measurements necessary to image an object. The important advantages of detector subsampling over view-angle subsampling is that the former enables one to measure or reduce scattered radiation. While many photons transiting an object under test travel directly from source to detector, there are also photons that scatter from within the object via various physical mechanisms, such as Compton and coherent scatter. These scattered photons reach the detectors by passing through a non-direct trajectory.

In many applications, scatter is a dominant source of noise, such as in medical scans using cone beam CT (CBCT). Reducing scatter by a non-continuous illumination can increase signal-to-noise ratio and therefore improve the quality of reconstructed images.

In some applications, such as security applications, however, the scattered photons can be exploited to derive additional information about the molecular structure of the imaged object, which enables one to identify potentiality dangerous substances.

Figure 10:
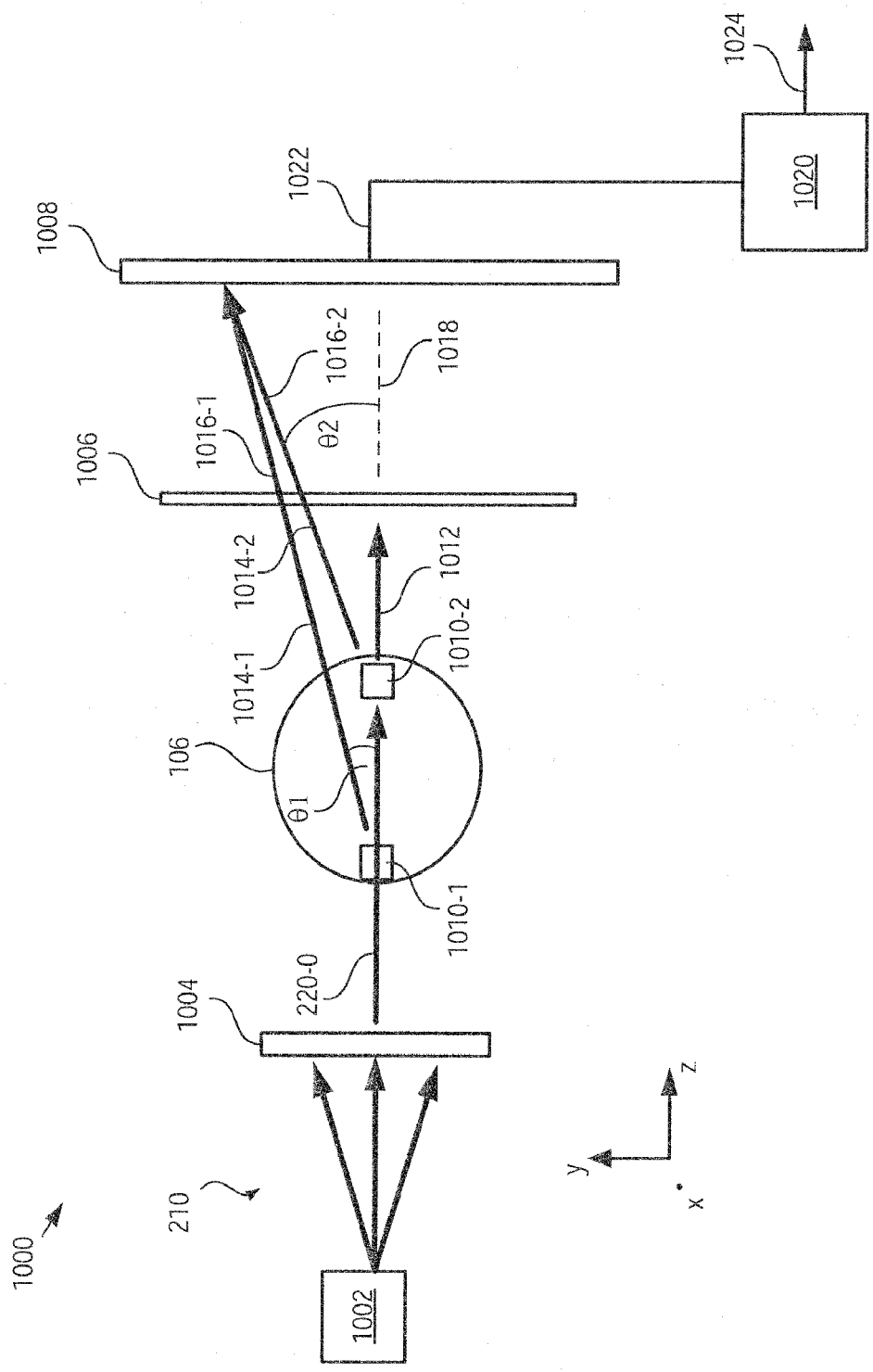
FIG. 10 depicts a schematic drawing of a side view of an imaging system in accordance with a third embodiment of the present invention.

FIG. 10 depicts a schematic drawing of a side view of an imaging system in accordance with a third embodiment of the present invention. System 1000 includes source 1002, coded apertures 1004 and 1006, detector array 1008, and processor 208.

Source 1002 is analogous to source 202, described above; source 1002 emits cone 210 such that it comprises x-ray radiation.

Coded aperture 1004 is analogous to coded aperture 204. Coded aperture 1004 restricts the radiation in cone 210 to a set of discontinuous discrete rays. For clarity, only one of the illumination rays passed by coded aperture 1004 is shown—principle ray 220-0, which propagates along principle axis 1018.

As principle ray 220-0 passes through object 106, it interacts with object elements 1010-1 and 1010-2. Each object element scatters principle ray 220-0 into transmitted primary beam 1012, along principal axis 1018, and scatter radiation 1014-1 and 1014-2 (referred to, collectively, as scatter radiation 1014). Scatter radiation 1014 is scattered in the forward direction as shown. Scatter radiation 1014-1 and 1014-2 scatter at angles θ1 to θ2, respectively, with respect to principal axis 1018. One skilled in the art will recognize that the magnitude of angles □1 to □2 is based on the material composition of object elements 1010-1 and 1010-2.

In most practical systems, object 106 includes many more than two object elements along the path of principle ray 220-0. As a result, more than two scatter radiation signals are typically generated; however, for the purposes of clarity in this discussion, only two scatter radiation signals (i.e., scatter radiation 1014-1 and 1014-2) are described.

As scatter radiation 1014-1 and 1014-2 passes through coded aperture 1006, they are encoded with its sampling structure, which is defined by the spatial features of coded aperture 1006. The encoded radiation is indicated as modulated radiation 1016-1 and 1016-2, respectively (referred to, collectively, as modulated radiation 1016).

Figure 11:
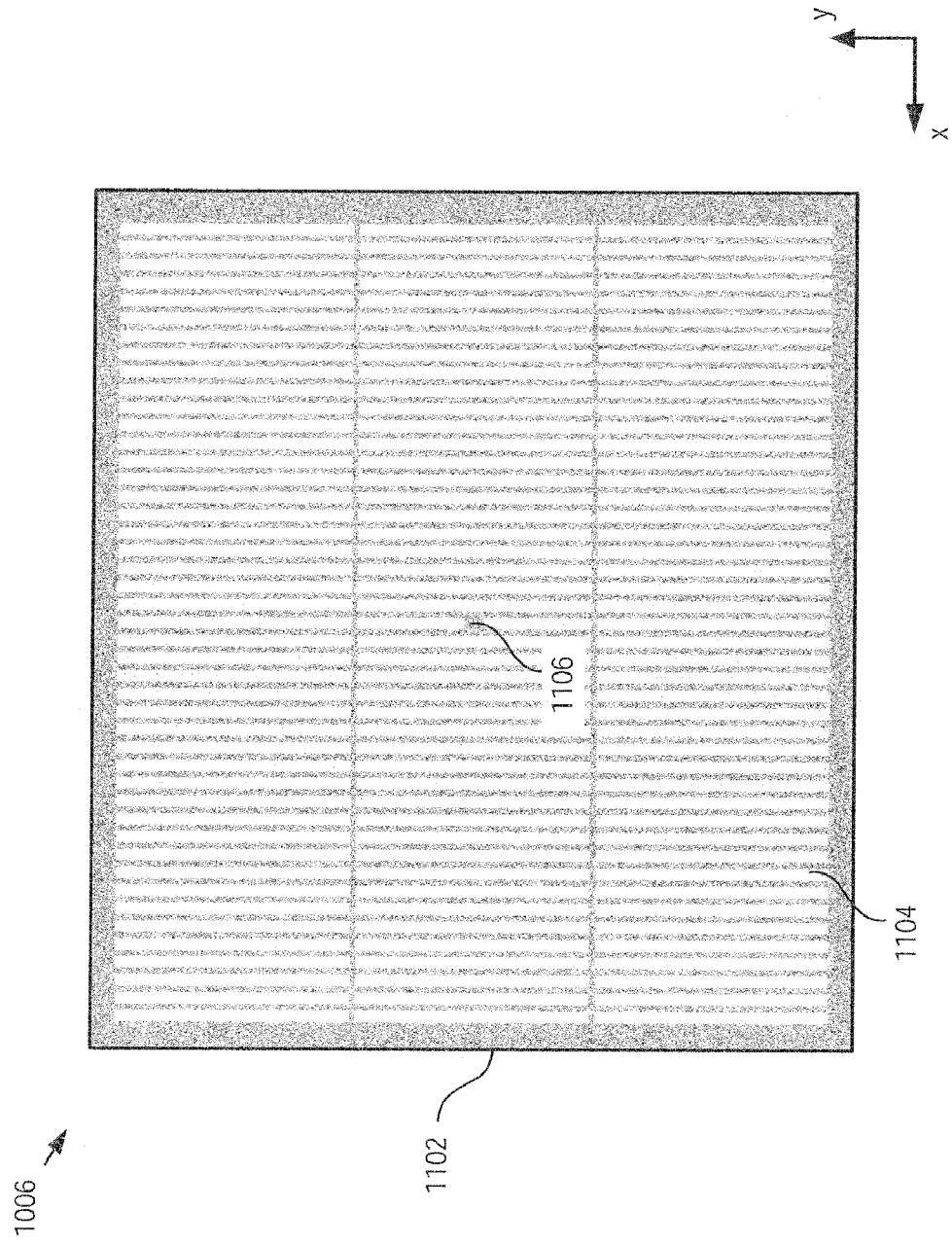
FIG. 11 depicts a schematic drawing of a representative coded aperture in accordance with the third embodiment of the present invention.

FIG. 11 depicts a schematic drawing of a representative coded aperture in accordance with the third embodiment of the present invention. Coded aperture 1006 comprises frame 1102, apertures 1104, and blocker 1106. In contrast with previous art, coded aperture 1006 includes a code (i.e., an arrangement of apertures 1104) that is periodic. As a result, aperture 1006 enables separable estimation of object density and scatter angle versus range (which is encoded as magnification).

Frame 1102 is a lead sheet whose thickness is suitable for blocking transmission of scatter radiation and sufficient mechanical strength to avoid warping or sagging under its own weight when oriented in the x-y plane.

Apertures 1104 are openings having a width and height suitable for encoding a spatial code onto scatter radiation 1014-1 and 1014-2. Apertures 1104 are arranged in an arrangement that is periodic in each of the x- and y-dimensions. In some embodiments, apertures 1104 are periodic in only one of the x- and y-dimensions. In some embodiments, apertures 1104 are not periodic.

It will be clear to one skilled in the art, after reading this Specification, that the pattern of coded aperture 1006 is a matter of design choice based on the particular class of objects to be scanned.

Blocker 1106 is a feature located substantially in the center of coded aperture 1006 to block transmitted primary beam 101012 from passing to detector 1008.

Detector 1008 is a two dimensional array of amorphous-silicon indirect cesium iodide x-ray detectors. The lateral extent and position of detector 1008, relative to source 1002 and object 106, is suitable for receiving the complete diffraction pattern of modulated radiation 1016. In some embodiments, detector 1008 comprises detectors other than amorphous-silicon indirect cesium iodide x-ray detectors.

Although the third embodiment comprises a system for forming an image based on modulated scattered x-ray radiation from an object, it will be clear to one skilled in the art, after reading this Specification, how to specify, make, and use alternative embodiments of the present invention that form images based on coded-aperture-modulated radiation other than scattered x-ray radiation, such as modulated fluorescence signals, and the like.

A method suitable for generating a three-dimensional estimation of the structure and composition of an object typically includes the operations of method 300, described above, as well as additional operation wherein processor 1020 reconstructs the composition of object 106 based on signal 1022 from detector array 1008.

In order to reconstruct the composition of object 106, processor 1020 employs a longitudinal forward model to classify and locate any objects along axis 1018, as well as other illumination rays transmitted through object 106. Processor 1020 estimates the coherent scatter properties of object 106 based on a modulated image formed on detector array 1008 by modulated radiation 1016, as well as the intensity of illumination rays 220 and the aperture pattern of coded aperture 1006. It should be noted that spectral filters can also be included in system 1000 to enable further characterization of object 106 based on its spectral characteristics.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A method for imaging an object, the method comprising:
    performing a first measurement of a physical phantom with a continuous illumination pattern;
    selecting a first set of illumination rays that are discrete and non-continuous, wherein the first set of illumination rays are selected based on the first measurement;
    interrogating the object with the first set of illumination rays, wherein the first set of illumination rays are generated by operations comprising:
        (i) generating a second set of illumination rays that is a continuous set of illumination rays; and
        (ii) filtering the second set of illumination rays at a coded aperture to prevent at least one illumination ray of the second set thereof from interrogating the object;

generating a dataset that includes values for the attenuation of each illumination ray of the first set thereof, the attenuation being based on the structure of the object along the path of the illumination ray; and reconstructing an image of the object based on the dataset.

2. The method of claim 1 wherein the first set of illumination rays includes illumination rays generated by a source at each of a plurality of source locations relative to the object.

3. The method of claim 2 wherein the plurality of source locations is determined randomly.

4. The method of claim 2 wherein the plurality of source locations are arranged uniformly about the object.

5. A method for imaging an object, the method comprising:
   performing a first measurement of a physical phantom with a continuous illumination pattern;
   selecting a first set of illumination rays that are discrete and non-continuous, wherein the first set of illumination rays are selected based on the first measurement;
   interrogating the object with the first set of illumination rays, wherein the first set of illumination rays are generated by operations comprising:
      (i) interrogating the object with a second set of illumination rays that is a continuous set of illumination rays that includes the first set of illumination rays; and
      (ii) subsampling the second set of illumination rays to select only the first set of illuminations rays for detection;
   generating a dataset that includes values for the attenuation of each illumination ray of the first set thereof, the attenuation being based on the structure of the object along the path of the illumination ray; and
   reconstructing an image of the object based on the dataset.

6. The method of claim 5 wherein the first set of illumination rays subsampled is selected randomly.

7. The method of claim 1 further comprising:
   imparting a spatial code on scatter radiation received from the object, wherein the spatial code is imparted by passing the scatter radiation through a coded aperture that includes a first plurality of openings whose arrangement is defined by a first pattern code, wherein the scatter radiation is based on at least one illumination ray of the first set thereof;
   detecting at least a portion of the encoded scatter information; and
   estimating a material property of the object based on the detected encoded scatter information.

8. A system for forming an image of an object, the system comprising:
   a source of radiation, the source being operative for providing a continuous illumination pattern;
   a first coded aperture that converts the continuous illumination pattern into a first set of illumination rays that are discrete and non-continuous, wherein the first set of illumination rays are selected based on a first measurement of a physical phantom using the continuous illumination pattern, and wherein the first coded aperture includes a first plurality of openings arranged in a first pattern code that is dimensioned and arranged to convert the continuous illumination pattern into the first set of illumination rays;
   a plurality of detectors, each detector of the plurality thereof being operative for detecting a different one of the first set of illumination rays; and
   a processor that is operative for determining the attenuation of each of the set of illumination rays due to interaction with the object.

9. The system of claim 8 further comprising a stage operative for changing the relative orientation between the source and the object.

10. The system of claim 9, wherein the stage is further operative for randomly selecting each of a plurality of relative orientations between the source and object.

11. The system of claim 9, wherein the stage is further operative for positioning the source in each of a plurality of positions about the object, and wherein the plurality of positions are uniformly distributed about the object.

12. The system of claim 8 further comprising a second coded aperture that is operative for imparting a spatial code on scatter radiation received from the object, the second coded aperture including a second plurality of openings that pass scatter radiation such that it is substantially unchanged.

13. The method of claim 1 further comprising selecting a first aperture code for the coded aperture, wherein the first aperture code is based on the first measurement of the physical phantom.

14. The method of claim 13 further comprising:
   performing a plurality of measurements of the physical phantom that includes the first measurement; and
   determining a set of aperture codes suitable for use in the coded aperture, wherein each aperture code of the set thereof is based on a different measurement of the plurality thereof;
   wherein the first aperture code is selected from the set of aperture codes.

15. The method of claim 12 wherein the process is further operative for estimating a material property of the object based on the encoded scatter information.

* * * * *